(12) United States Patent
Koehler et al.

(10) Patent No.: US 7,782,997 B2
(45) Date of Patent: Aug. 24, 2010

(54) RECONSTRUCTION ALGORITHM FOR OBJECT POINT OUTSIDE THE SCAN-FIELD-OF-VIEW

(75) Inventors: Thomas Koehler, Noderstedt (DE); Peter Forthmann, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 252 days.

(21) Appl. No.: 11/994,700

(22) PCT Filed: Jul. 4, 2006

(86) PCT No.: PCT/IB2006/052247

§ 371 (c)(1), (2), (4) Date: Jan. 4, 2008

(87) PCT Pub. No.: WO2007/004195

PCT Pub. Date: Jan. 11, 2007

(65) Prior Publication Data

US 2008/0226016 A1    Sep. 18, 2008

(30) Foreign Application Priority Data

Jul. 5, 2005   (EP) .................. 05106086

(51) Int. Cl.
*A61B 6/00*    (2006.01)
(52) U.S. Cl. .......................................... 378/4
(58) Field of Classification Search ....... 378/4
See application file for complete search history.

(56) References Cited

U.S. PATENT DOCUMENTS

| | | | |
|---|---|---|---|
| 4,670,892 A * | 6/1987 | Abele et al. ............. | 378/4 |
| 2002/0186809 A1* | 12/2002 | Flohr et al. ............. | 378/4 |
| 2004/0066911 A1 | 4/2004 | Hsieh et al. | |
| 2006/0034417 A1* | 2/2006 | Katsevich ............... | 378/4 |
| 2006/0262894 A1* | 11/2006 | Bernhardt et al. ....... | 378/4 |
| 2006/0291611 A1* | 12/2006 | Pack et al. ............. | 378/4 |
| 2007/0253523 A1* | 11/2007 | Zamyatin ............... | 378/4 |

FOREIGN PATENT DOCUMENTS

| | | |
|---|---|---|
| EP | 0403209 A1 | 12/1990 |
| WO | 2004072905 A1 | 8/2004 |

OTHER PUBLICATIONS

Noo, F., et al.; A two-step Hilbert transform method for 2D image reconstruction; 2004; Phys. Med. Biol.; 49:3903-3923.
Pack, J. D., et al.; Cone-Beam Reconstruction Using the Backprojection of Locally Filtered Projections; 2005; IEEE Trans. on Medical Imaging; 24(1)70-85.
Quinn, E. T.; Tomographic reconstructions from incomplete data-numerical inversion of the exterior Radon transform; 1988; Inverse Problems; 4:867-876.

* cited by examiner

*Primary Examiner*—Edward J Glick
*Assistant Examiner*—Alexander H Taningco

(57) ABSTRACT

CT scanners have a certain scan-field-of-view defined by the fan-angle of the system. According to an exemplary embodiment of the present invention, object points outside the scan-field-of-view may be reconstructed on the basis of a system of linear equations which may be solved iteratively and with reasonable effort. Therefore, explicit regularization techniques may be applied to recover the unknown object function.

15 Claims, 2 Drawing Sheets

RECONSTRUCTION ALGORITHM FOR OBJECT POINT OUTSIDE THE SCAN-FIELD-OF-VIEW

The present invention relates to the field of X-ray imaging. In particular, the present invention relates to a computer tomography apparatus for examining an object of interest, to a method of examining an object of interest, an image processing device, a computer-readable medium and a program element.

Computed tomography (CT) scanners have a certain scan-field-of-view (scan-fov) which is defined by the fan-angle of the system. The scan-fov is defined as the region, which is illuminated during the entire scan and it is typically of the order of 500 mm in diameter. The scan-fov is the region, in which exact or good approximate reconstruction can be achieved. However, sometimes a relevant portion of the object is outside the scan-fov. In particular, for combined system such as PET/CT (Positron Emission Tomography/Computed Tomography) or SPECT/CT (Single Photon Emission Computed Tomography/Computed Tomography), estimated attenuation outside the scan-fov must be provided by the reconstruction in order to allow for a reasonable attenuation correction in a subsequent emission scan.

It may be desirable to provide an improved reconstruction outside the scan-field-of-view.

According to an exemplary embodiment of the present invention, a computer tomography apparatus for examination of an object of interest may be provided, the computer tomography apparatus comprising a reconstruction unit, the reconstruction unit being adapted for reconstructing an object point outside a scan-field-of-view on the basis of a system of linear equations, wherein the system of linear equations is only defined for object points outside the scan-field-of-view.

Thus, according to this exemplary embodiment of the present invention, the unknown object function may be recovered by solving the system of linear equations without the use of projection data resulting from object points inside the scan-fov. Solving the system of linear equations may be performed efficiently, which may result in a fast and yet high quality reconstruction of object points outside the scan-field-of-view.

According to another exemplary embodiment of the present invention, the object point outside the scan-fov is located inside a triangular region for which region the system of linear equations is defined.

This region may be covered completely by tangents to the scan-fov and may be relatively small, such that a highly accurate reconstruction of object points inside that triangular region may be performed on the basis of information relating to the tangents.

According to another exemplary embodiment of the present invention, the reconstruction of the object point outside the scan-field-of-view is performed without information about an attenuation inside the scan-field-of-view.

According to another exemplary embodiment of the present invention, the reconstruction of the object point outside the scan-field-of-view is an iterative reconstruction.

Thus, the reconstruction accuracy may be improved by increasing the number of iterative reconstruction steps.

According to another exemplary embodiment of the present invention, the reconstruction unit is further adapted for applying an explicit regularization technique for recovering an unknown object function.

According to another exemplary embodiment of the present invention, the system of linear equations is based on a back-projection of differentiated line-integrals.

According to another exemplary embodiment of the present invention, the system of linear equations may be based on a Pack reconstruction and may be defined by $$\frac{1}{\pi} b_a(\vec{x}, \lambda_1, \lambda_2) = K^*(\vec{\omega}(\lambda_2), \vec{x}), \vec{x}) - K^*(\vec{\omega}(\lambda_1), \vec{x}), \vec{x})$$

wherein $b_a(\vec{x},\lambda_1,\lambda_2)$ is a result of the back-projection of differentiated data from source position $\lambda_1$ to $\lambda_2$ plus two boundary terms at the object point location $\vec{x}$, and wherein $K^*$ is an inverse Hilbert transform of an image along a line $\vec{\omega}$.

The Pack reconstruction is described in J. Pack, F. Noo, and R. Clackdoyle, IEEE Trans. Med. Imag., 24(1), January 2005, pp. 70-85, which is hereby incorporated by reference.

According to another exemplary embodiment of the present invention, the computer tomography apparatus may comprise an electromagnetic radiation source adapted for moving along a helical source path and for emitting electromagnetic radiation source to the object of interest. Furthermore, the CT apparatus may comprise a collimator arranged between the electromagnetic radiation source and detecting elements, wherein the collimator is adapted for collimating an electromagnetic radiation beam emitted by the electromagnetic radiation source to form a cone-beam.

The computer tomography apparatus according to the invention may be applied as a baggage inspection apparatus, a medical application apparatus, a material testing apparatus or a material science analysis apparatus. A field of application of the invention may be baggage inspection, since the defined functionality allows a secure and reliable analysis of the content of a baggage item, even if the content is outside the scan-field-of-view. This may allow for a detection of suspicious content outside the scan-fov.

Such an apparatus or method in accordance with an exemplary embodiment of the present invention may create a high quality automatic system that may automatically recognize certain types of materials and, if desired, trigger an alarm in the presence of dangerous materials.

According to another exemplary embodiment of the present invention, a method of examining an object of interest with a computer tomography apparatus may be provided, the method comprising the step of reconstructing an object point outside a scan-field-of-view on the basis of a system of linear equations.

This may provide for an efficient and highly accurate reconstruction of object points outside the scan-fov.

According to another exemplary embodiment of the present invention, a method is provided in which the object point is located outside the scan-field-of-view but inside a triangular region for which the system of linear equations is defined. Furthermore, the reconstruction of the object point outside the scan-fov is performed without reconstructing the attenuation inside the scan-fov, wherein the reconstruction is an iterative reconstruction.

According to another exemplary embodiment of the present invention, an image processing device for examining an object of interest with a computer tomography apparatus may be provided, the image processing device comprising a memory for storing projection data and a reconstruction unit adapted for carrying out the above-mentioned method steps.

Furthermore, according to another exemplary embodiment of the present invention, a computer-readable medium may be provided, in which a computer program of examining an object of interest with a computer tomography apparatus is stored which, when being executed by a processor, is adapted to carry out the above-mentioned method steps.

The present invention also relates to a program element of examining an object of interest, which, when being executed by a processor, is adapted to carry out the above-mentioned method steps. The program element may be stored on a computer-readable medium and may be loaded into working memories of a data processor. The data processor may thus be equipped to carry out exemplary embodiments of the methods of the present invention. The computer program may be written in any suitable programming language, such as, for example, C++ and may be stored on a CD-ROM or any other computer-readable medium. Also, the computer program may be available from a network, such as the WorldWideWeb, from which it may be downloaded into image processing units or processors, or any suitable computers.

It may be seen as the gist of an exemplary embodiment of the present invention, that a reconstruction scheme of an object point outside a scan-field-of-view is provided by solving a system of linear equations. According to an exemplary embodiment of the present invention, the system of linear equations is based on the Pack reconstruction, therefore providing for an exact back-projection filtering type reconstruction for object points inside the scan-fov and for an efficient and accurate reconstruction for object points outside the scan-fov.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements may be provided with the same reference numerals.

Figure 1:
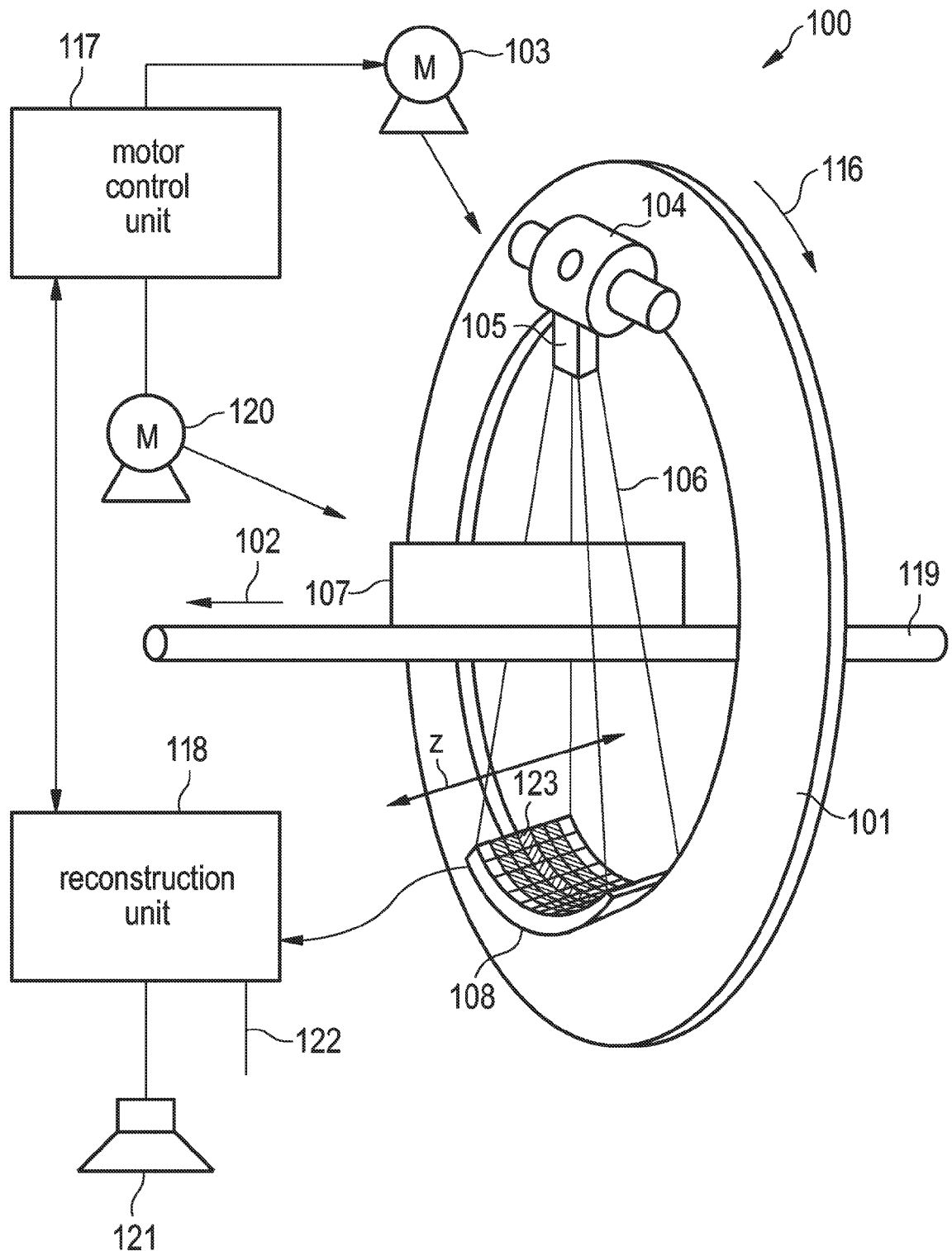
FIG. 1 shows a simplified schematic representation of a CT scanner system according to an exemplary embodiment of the present invention.

FIG. 1 shows an exemplary embodiment of a CT scanner system according to an exemplary embodiment of the present invention. With reference to this exemplary embodiment, the present invention will be described for the application in baggage inspection. However, it should be noted that the present invention is not limited to this application, but may also be applied in the field of medical imaging, or other industrial applications, such as material testing.

The computer tomography apparatus 100 depicted in FIG. 1 is a cone-beam CT scanner. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits a polychromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the centre of the gantry 101, i.e. in an examination region of the CT scanner, and impinges onto the detector 108.

As may be taken from FIG. 1, the detector 108 is arranged on the gantry 101 opposite to the source of radiation 104, such that the surface of the detector 108 is covered by the cone-beam 106. The detector 108, which is depicted in FIG. 1, comprises a plurality of detector elements 123 each capable of detecting, in an energy-resolving manner X-rays or individual photons which have penetrated the object of interest 107.

During a scan of the object of interest 107, the source of radiation 104, the aperture system 105 and the detector 108 are rotated along the gantry 101 in the direction indicated by arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 may be an item of baggage or a patient which is disposed on a conveyor belt 119. During the scan of the object of interest 107, while the gantry 101 rotates around the item of baggage 107, the conveyor belt 119 displaces the object of interest 107 along a direction parallel to the rotational axis 102 of the gantry 101. By this, the object of interest 107 is scanned along a helical scan path. The conveyor belt 119 may also be stopped during the scans to thereby measure single slices. Instead of providing a conveyor belt 119, for example, in medical applications where the object of interest 107 is a patient, a movable table may be used. However, it should be noted that in all of the described cases it may also be possible to perform a circular scan, where there is no displacement in a direction parallel to the rotational axis 102, but only the rotation of the gantry 101 around the rotational axis 102.

The detector 108 may be connected to the calculation unit 118. The calculation unit 118 may receive the detection result, i.e. the read-outs from the detector elements 123 of the detector 108 and may determine a scanning result on the basis of the read-outs. Furthermore, the calculation unit 118 communicates with the motor control unit 117 in order to coordinate the movement of the gantry 101 with motors 103 and 120 with the conveyor belt 119.

The reconstruction unit 118 may be adapted for reconstructing an image from read-outs of the detector 108 by reconstructing an object point outside a scan-field-of-view on the basis of a system of linear equations, according to an exemplary embodiment of the present invention. A reconstructed image generated by the reconstruction unit 118 may be output to a display (not shown in FIG. 1) via an interface 122.

The reconstruction unit 118 may be realized by a data processor to process read-outs from the detector elements 123 of the detector 108.

Furthermore, as may be taken from FIG. 1, the reconstruction unit 118 may be connected to a loudspeaker 121, for example, to automatically output an alarm in case of the detection of suspicious material in the item of baggage 107.

The examination apparatus 100 for examination of the object of interest 107 includes the detector 108 having the plurality of detecting elements 123 arranged in a matrix-like manner, each being adapted to detect X-rays. Furthermore, the computer tomography apparatus 100 comprises the determination unit or reconstruction unit 118 adapted for reconstructing an image of the object of interest 107.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. The detecting elements 123 form a multi-slice detector array 108. The computer tomography apparatus 100 may be configured as a medical imaging apparatus or baggage inspection apparatus.

Figure 2:
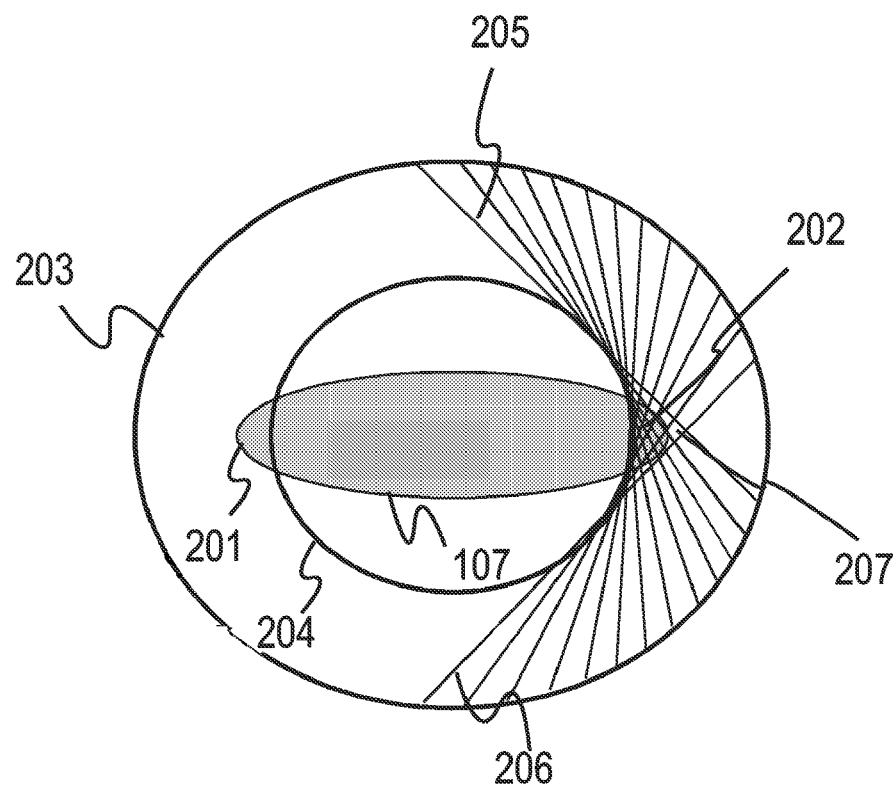
FIG. 2 shows a schematic representation of a two-dimensional CT scan with partially truncated data.

FIG. 2 shows a schematic representation of a two-dimensional CT scan with partially truncated data. As may be seen from FIG. 2, the object of interest 107 only partially lies inside the scan-fov defined by circle 204. The left end 201 of the object of interest 107 and the right end 202 of the object of interest 107 both lie outside the scan-fov.

The object of interest 107 lies more or less in the middle of the source path 203 along which the source of electromagnetic radiation 104 (not depicted in FIG. 2) moves during inspection of the object of interest 107. The source path 203 may be a helical source path or of any other geometry. For example, the CT scanner system 100 of FIG. 1 may be applied in the form of a C-arm scanner system.

As may be seen from FIG. 2, the right end 202 of the object of interest 107, which lies outside the scan-fov, lies inside a triangular shaped region 207, which is defined by a group of tangents 205, 206 to the scan-fov.

Currently, it is detected, whether the projection data is truncated or not, i.e. whether a part of the object has been outside the scan-fov during the acquisition of projection data or not. In case of a detected truncation, the projection data is extended by means of extrapolation. In some methods for extrapolation, a simple model is used, for example by assuming that the object is a cylinder. Furthermore, the Fourier-slice theory may be used to ensure a proper total attenuation for each projection.

However, this procedure is purely heuristic.

By applying a reconstruction scheme according to the Pack reconstruction which has been mentioned above, a back-projection filtering style reconstruction method for computer tomography may be provided. One result according to the Pack reconstruction scheme is the following relation:

$$\frac{1}{\pi} b_a(\vec{x}, \lambda_1, \lambda_2) = K^*(\vec{\omega}(\lambda_2, \vec{x}), \vec{x}) - K^*(\vec{\omega}(\lambda_1, \vec{x}), \vec{x}) \quad \text{(Equation 1)}$$

wherein $b_a(\vec{x}, \lambda_1, \lambda_2)$ is the result of the back-projection of differentiated data from source position $\lambda_1$ to $\lambda_2$ plus two boundary terms at the object point location $\vec{x}$. $K^*$ denotes the inverse Hilbert transform of the image along the line $\vec{\omega}$:

$$K^*(\vec{\omega}(\lambda, \vec{x}), \vec{x}) = -\int_{-\infty}^{\infty} \frac{1}{\pi t} f(\vec{x} + t\vec{\omega}(\lambda, \vec{x})) dt$$

According to the Pack reconstruction scheme, this relation is exploited by selecting the back-projection interval such, that the two lines $\vec{\omega}(\lambda_1, \vec{x})$ and $\vec{\omega}(\lambda_2, \vec{x})$ are anti-parallel and a 1D inverse Hilbert transform can be used to reconstruct the attenuation at the object point location $\vec{x}$.

It may not be possible to achieve this for object points outside the scan-fov, because object points are inside the fan over less than 180°. FIG. 2 illustrates the geometry and the location of the lines $\vec{\omega}(\lambda, \vec{x})$ for a two-dimensional case.

It can be inferred from the projection data itself that the part of the object on the right hand side 202, which is outside the scan-fov, is confined in a nearly triangular shaped region 207. This region 207 is covered completely by tangents 205, 206, etc. to the scan-fov.

It should be noted that this region may be relatively small. Equation (1) defines a system of linear equations for object function inside this triangular region 207. No information about the attenuation inside the scan-field-of-view is required in order to solve this system. Since the region is typically rather small, an iterative reconstruction may be performed with reasonable effort. Compared to heuristic techniques, explicit regularization techniques may be applied for recovering the unknown object function.

The system of linear equations may be written as $$Ax=y$$

where x is a vector of unknown values of the object function $f$, sampled at discrete spatial locations $r_i$, A is the discrete version of the two Hilbert-transformation over the yet unknown image outside the scan fov, and y is a vector containing the back-projected differentiated data at the same locations $r_i$. Since both, the right hand side y and the vector of unknowns x are located on the same grid, A is a square matrix, thus one and only one solution exists if A has only positive singular values, which can be obtained by direct inversion if A is rather small or by iterative methods like ART if A is large. However, in the presence of noise, it may be advantageous to apply some regularization techniques: Here, a modified system of equations is solved, for instance the minimum of $$\Delta = \|Ax-y\|^2 + R(x)$$

is searched for. Here R is a roughness penalty, which forces the solution to be smooth. Furthermore, the roughness penalty can be used to enforce a continuous object function across the boundary of the scan fov. Remember that one goal is to recover the object function $f$ inside and outside the scan-fov and that $f$ is reconstructed inside the scan fov using an analytic reconstruction method. Now, a solution of the reconstruction outside the scan fov may be forced to fit smoothly to the analytic reconstruction inside the scan fov. This may be achieved for example if the roughness penalty contains terms of the form $\|x_i - n(x_i)\|^2$ for all unknowns $x_i$ which have a neighbouring grid point inside the scan-fov. The value $n(x_i)$ of the object function inside the scan-fov is taken from the analytic reconstruction. Other popular choices for the roughness, which can be added to the aforementioned penalty are $$R_1 = \|x_i\|^2$$

or $$R_2 = \|\Delta x_i\|^2$$

where $\Delta$ is a discete version of the Laplace operator, or $$R_3 = \|\Delta x_i\|_1$$

where $\|\ \|_1$ is the $L_1$-norm of the vector (sum of absolute values).

Figure 3:
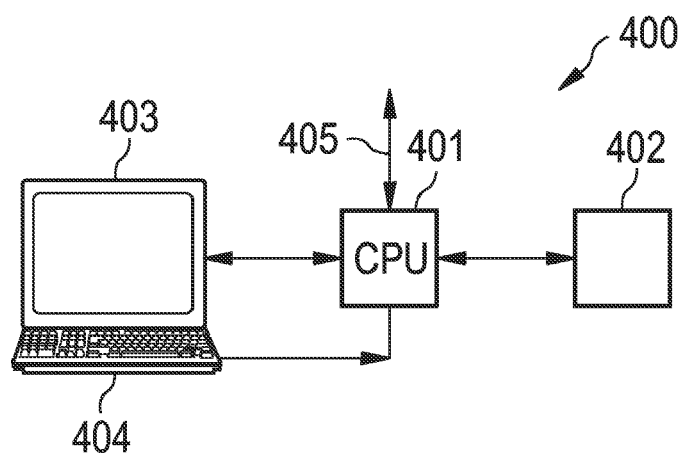
FIG. 3 shows an exemplary embodiment of an image processing device according to the present invention, for executing an exemplary embodiment of a method in accordance with the present invention.

FIG. 3 depicts an exemplary embodiment of an image processing device according to the present invention for executing an exemplary embodiment of the method in accordance with the present invention. The image processing device 400 depicted in FIG. 3 comprises a central processing unit (CPU) or image processor 401 connected to a memory 402 for storing an image depicting an object of interest, such as a patient or an item of baggage. The data processor 401 may be connected to a plurality of input/output network for diagnosis devices, such as a CT device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 3.

Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

The examination of an object of interest according to the present invention may allow for an high quality reconstruction algorithm for object point outside the scan-field-of-view.

Exemplary embodiments of the invention may be sold as a software option to CT scanner console, imaging work stations or PACS work stations.

It should be noted that the term "comprising" does not exclude other elements or steps and the "a" or "an" does not exclude a plurality and that a single processor or system may fulfill the functions of several means or units recited in the claims. Also elements described in association with different embodiments may be combined.

It should also be noted, that any reference signs in the claims shall not be construed as limiting the scope of claims.

The invention claimed is:

1. A computer tomography apparatus for examination of an object of interest, the computer tomography apparatus comprising a reconstruction unit, the reconstruction unit being adapted for:
   reconstructing an object point outside a scan-field-of-view on the basis of a system of linear equations;
   wherein the system of linear equations is only defined for object points outside the scan-field-of-view.

2. The computer tomography apparatus of claim 1,
   wherein the object point outside the scan-field-of-view is located inside a triangular region for which the system of linear equations is defined.

3. The computer tomography apparatus of claim 1,
   wherein the reconstruction of the object point outside the scan-field-of-view is performed without information about an attenuation inside the scan-field-of-view.

4. The computer tomography apparatus of claim 1,
   wherein the reconstruction of the object point outside the scan-field-of-view is an iterative reconstruction.

5. The computer tomography apparatus of claim 1, the reconstruction unit is further adapted for:
   applying an explicit regularization technique for recovering an unknown object function.

6. The computer tomography apparatus of claim 1,
   wherein the system of linear equations is based on a back-projection of differentiated line-integrals.

7. The computer tomography apparatus of claim 1,
   wherein the system of linear equations is based on a Pack reconstruction and is defined by $$\frac{1}{\pi} b_a(\vec{x}, \lambda_1, \lambda_2) = K^*(\vec{\omega}(\lambda_2, \vec{x}), \vec{x}) - K^*(\vec{\omega}(\lambda_1, \vec{x}), \vec{x})$$

wherein $b_a(\vec{x}, \lambda_1, \lambda_2)$ is a result of the back-projection of differentiated data from source position $\lambda_1$ to $\lambda_2$ plus two boundary terms at the object point location x; and
wherein $K^*$ is an inverse Hilbert transform of an image along a line to.

8. The computer tomography apparatus of claim 1, further comprising:
   an electromagnetic radiation source moving along a helical scan path around the object of interest;
   a collimator arranged between the electromagnetic radiation source and detecting elements;
   wherein the collimator is adapted for collimating an electromagnetic radiation beam emitted by the electromagnetic radiation source to form a cone-beam.

9. The computer tomography apparatus of claim 1,
   wherein the detecting elements form a single-slice detector array.

10. The computer tomography apparatus of claim 1,
    wherein the detecting elements form a multi-slice detector array.

11. The computer tomography apparatus of claim 1, configured as one of the group consisting of a baggage inspection apparatus, a medical application apparatus, a material testing apparatus and a material science analysis apparatus.

12. A method of examining of an object of interest with a computer tomography apparatus, the method comprising the step of:
    using a processor to reconstruct an object point outside a scan-field-of-view on the basis of a system of linear equations;
    wherein the system of linear equations is only defined for object points outside the scan-field-of-view.

13. The method of claim 12,
    wherein the object point outside the scan-field-of-view is located inside a triangular region for which the system of linear equations is defined;
    wherein the reconstruction of the object point outside the scan-field-of-view is performed without information about an attenuation inside the scan-field-of-view;
    wherein the reconstruction of the object point outside the scan-field-of-view is an iterative reconstruction.

14. An image processing device for examining an object of interest with a computer tomography apparatus, the image processing device comprising:
    a memory for storing projection data;
    a reconstruction unit, being adapted for:
    reconstructing an object point outside a scan-field-of-view on the basis of a system of linear equations;
    wherein the system of linear equations is only defined for object points outside the scan-field-of-view.

15. A non-transitory computer-readable medium, in which a computer program of examining an object of interest with a computer tomography apparatus is stored which, when being executed by a processor, is adapted to carry out the steps of:
    reconstructing an object point outside a scan-field-of-view on the basis of a system of linear equations;
    wherein the system of linear equations is only defined for object points outside the scan-field-of-view.

* * * * *